(12) United States Patent
Lattner

(10) Patent No.: US 7,579,383 B2
(45) Date of Patent: Aug. 25, 2009

(54) FLUID BED METHANOL SYNTHESIS

(75) Inventor: James R. Lattner, LaPorte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 590 days.

(21) Appl. No.: 11/484,076

(22) Filed: Jul. 11, 2006

(65) Prior Publication Data

US 2007/0027220 A1 Feb. 1, 2007

Related U.S. Application Data

(60) Provisional application No. 60/703,025, filed on Jul. 27, 2005.

(51) Int. Cl.
*C07C 27/00* (2006.01)

(52) U.S. Cl. .................. 518/713; 518/700; 518/714

(58) Field of Classification Search .................. 518/700, 518/713, 714
See application file for complete search history.

(56) References Cited

U.S. PATENT DOCUMENTS

| | | | |
|---|---|---|---|
| 4,956,392 A | 9/1990 | Saito et al. | |
| 5,216,034 A | 6/1993 | Sie | |
| 5,512,599 A | 4/1996 | Hiramatsu et al. | |
| 2004/0076554 A1* | 4/2004 | Kuechler et al. | 422/139 |
| 2006/0182673 A1* | 8/2006 | Hensman | 422/198 |

FOREIGN PATENT DOCUMENTS

GB   2 202 531   9/1988

* cited by examiner

*Primary Examiner*—Jafar Parsa

(57) ABSTRACT

This invention is directed to a process for making a methanol product from a synthesis gas (syngas) feed using a fluid bed reactor. Internal reactor heat transfer is balanced between feed preheat and catalyst bed temperature using appropriate backmixing of feed and catalyst. Backmixing can be appropriately controlled using a number of control points, including any one or more of superficial gas velocity, catalyst density in the reactor, reactor height to diameter ratio (preferably at least in the region of the dense catalyst bed), and catalyst particle size.

26 Claims, 2 Drawing Sheets

FLUID BED METHANOL SYNTHESIS

CROSS REFERENCE TO RELATED APPLICATIONS

This application claims the benefit of Provisional Application No. 60/703,025 filed Jul. 27, 2005, the disclosure of which is fully incorporated herein by reference.

FIELD OF THE INVENTION

This invention relates to the production of methanol. In particular, this invention relates to the production of methanol using a fluidized bed reactor.

BACKGROUND OF THE INVENTION

Current technology limits the size of a single train methanol plant to about 5000 t/day. There is incentive to increase the scale of methanol production to enable economic conversion of remote natural gas into a transportable form, either for fuel needs or for other processes such as methanol-to-olefins (MTO) processes. Such prospects may entail increasing methanol production on a scale of from 2 to 4 times current processes.

Many methanol synthesis reactor designs currently utilize some sort of external cooling that takes place as the reaction proceeds. See Appl, M., *Modern Production Technologies*, British Sulphur Publishing, London, 1997 ISBN 1 8733387 26 1. Generally, the external cooling takes place in one of two ways: (i) several adiabatic reactor beds in series with coolers in between stages, or (ii) cooling tubes located within the fixed reactor bed. Either of these methods results in a relatively complicated reactor design due to the need for integrated cooling. The reactor feed must be preheated, and then additional heat transfer surface is required to remove the heat of reaction.

U.S. Pat. No. 5,512,599 discloses an ultra-large scale reaction apparatus capable of producing 5,000 tons/day or more of methanol. The methanol can be synthesized by means of a fluidized bed reactor at a linear velocity of 0.51 m/sec. The fluidized bed catalytic reactor includes internal heat transfer tubes.

U.S. Pat. No. 5,216,034 discloses the use of multiple reactors in series for making methanol. The reactors include catalyst in a fluidized bed. Each reactor is equipped with at least one heat exchanger, an inlet for synthesis gas and an outlet for the reaction mixture. Each outlet is connected to a heat exchanger, which is connected to a gas/liquid (methanol) separator. The separator has an outlet for unconverted synthesis gas, and the outlet is connected to the next reactor in series.

U.S. Pat. No. 4,956,392 discloses a process for producing methanol. Synthesis gas feed is passed through a fluidized bed catalytic reactor at a superficial linear velocity of at leat 0.2 m/sec. Heat is recovered from the reaction by passing a heat transfer medium though a heat transmission tube in the reactor.

U.K. Patent No. GB 2 202 531 discloses a process for producing methanol or mixed alcohol from synthesis gas using a fluidized catalyst bed. Catalyst particles in the bed are contacted with the synthesis gas at a superficial linear velocity of at least 0.2 m/sec and a pressure of 40 to 200 atmospheres. A heat transmission tube is installed in the reactor.

What is needed is a reaction system that substantially reduces or eliminates the need for integrated heat transfer within the reaction zone. Such a system would be particularly beneficial if it were uncomplicated in design, or had other such advantages as having limited quench points, a relatively even temperature profile, and/or a high degree of mixing. In addition, the system should be easily scaled to very large capacities.

SUMMARY OF THE INVENTION

This invention provides a process for producing methanol using a fluidized bed reactor. In particular, the reactor system is uncomplicated in design, has limited quench points, a relatively even temperature profile, and a high degree of mixing. The reactor itself can be easily scaled to very large capacities. Such advantages are provided by balancing internal reactor heat transfer between feed preheat and catalyst bed temperature using appropriate backmixing of feed and catalyst.

According to one aspect of the invention, there is provided a process for making methanol product in a fluid bed reactor. The process comprises contacting a gas containing carbon monoxide and hydrogen with methanol synthesis catalyst in a fluidized bed to form methanol product. The contacting is performed by flowing the gas through a fluid bed reactor. Preferably, the gas contact within the reactor is at a superficial gas velocity of not greater than 2 meters per second. More preferably, the superficial gas velocity is at least 0.1 meter per second.

The fluidized bed is mixed to provide proper heat transfer. In one embodiment, proper mixing is provided within a reactor in which the fluidized bed has a catalyst bed height to diameter ratio of not greater than 10:1. The catalyst is separated from the methanol product in an upper portion of the reactor.

The catalyst is recycled for further use. In particular, the catalyst that is separated from the methanol product is returned to the fluidized bed for further contacting with feed gas.

It is not necessary that the reactor have any internal surface area. In one embodiment, the reactor has an internal heat exchange surface having a surface to volume ratio of not greater than 100 $m^{-1}$.

Preferably, the fluidized bed is in the dense phase. In particular, it is preferred that the fluidized bed is a dense phase fluidized bed maintained at a solids volume fraction of from 0.20 to 0.55.

In one embodiment, the fluidized bed is maintained at a temperature of from 150° C. to 350° C. Preferably, the gas feed flows into the reactor at a temperature of from 60° C. to 95° C. as one means to control fluid bed temperature. More preferably, the gas feed further contains $CO_2$, and the gas is contacted with the catalyst at a rate to control molar conversion of the CO and $CO_2$, based on the total amount of CO and $CO_2$ in the feed, in a range of from 30% to 55%. It is also preferred that the catalyst bed be maintained at a temperature differential of not greater than about 50° C.

The methanol synthesis catalyst can be any catalyst that is capable of catalyzing the conversion of synthesis gas components to methanol product in a fluidized bed reactor. In one embodiment, the methanol synthesis catalyst includes an oxide of at least one element selected from the group consisting of copper, silver, zinc, boron, magnesium, aluminum, vanadium, chromium, manganese, gallium, palladium, osmium and zirconium.

BRIEF DESCRIPTION OF THE DRAWINGS

An example of the invention is provided with reference to the attached Figures, wherein.

DETAILED DESCRIPTION OF THE INVENTION

Figure 1:
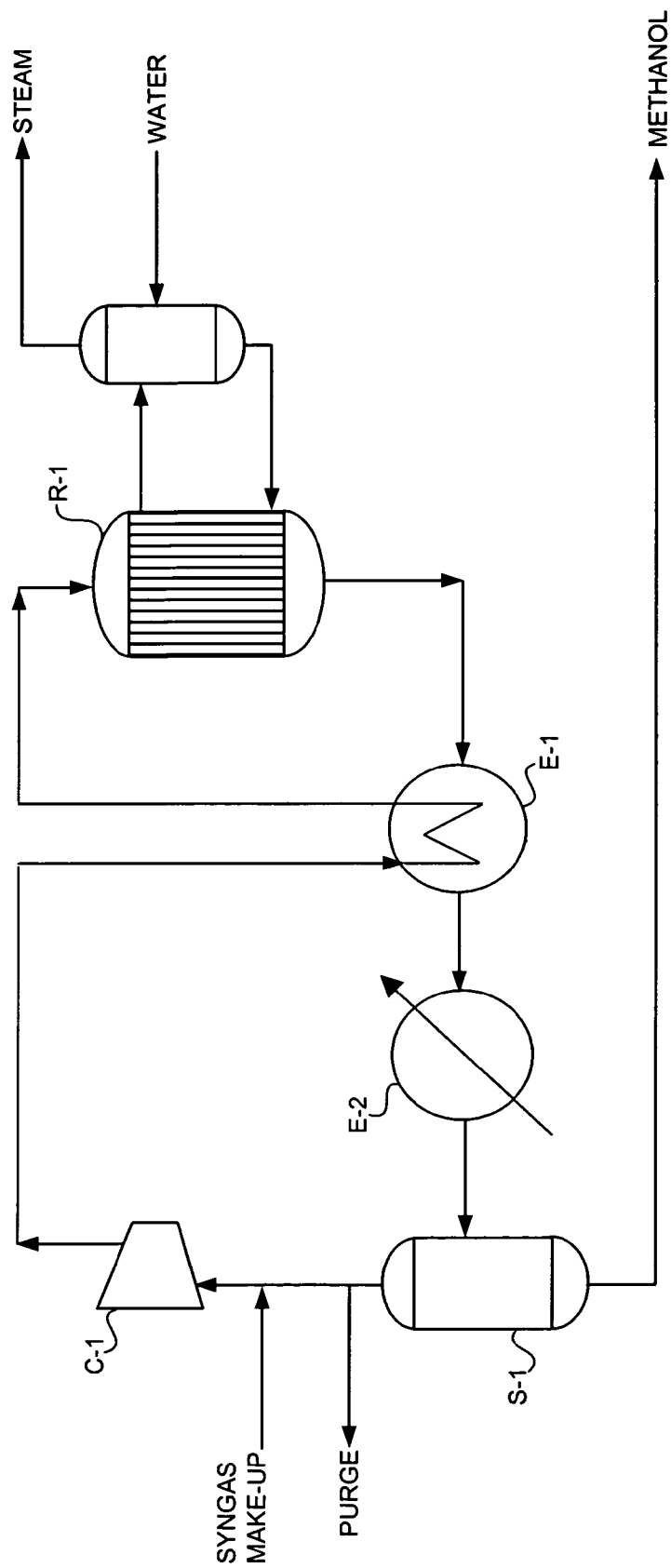
FIG. 1 shows a typical prior art design of a reactor system for producing methanol.

I. Balance of Heat Transfer Using a Fluidized Bed

This invention is directed to a process for making a methanol product from a synthesis gas (syngas) feed using a fluid bed reactor. The reactor is operated in the gas phase, with catalyst particles being fluidized in the reactor. Fluidization is controlled so that the catalyst particles in the reactor form a fluid phase in which the particles are well-mixed.

The process of making the methanol from syngas is an exothermic reaction, which means that the reaction gives off heat. The invention provides that the heat generated in the reactor by the exothermic reaction process is balanced so as to heat the feed up to a desired temperature to effectively control the dense bed temperature. This balance is such that little if any internal reactor cooling is needed. Preferably, the reactor needs no internal cooling means.

Internal reactor heat transfer is balanced between feed preheat and catalyst bed temperature using appropriate backmixing of catalyst. Backmixing of catalyst solids within the reactor distributes the heat generated from the exothermic reaction uniformly throughout the bed. The catalyst solids heated during the reaction are circulated back toward the feed zone, so that the feed is preheated with the heated solids. The use of catalyst solids to preheat the feed while simultaneously conducting the methanol synthesis reaction greatly simplifies the reaction system and reduces the amount of heat transfer surface required to control the process.

The reactor used in the invention can be of any type of reactor in which a dense phase fluidized bed can be maintained. Examples of such reactors are shown in *Fluidization Engineering*, D. Kunii and O. Levenspiel, Robert E. Krieger Publishing Company, New York, N.Y. 1977. Backmixing of catalyst in the reactor can be achieved through proper reactor design and selection of process variables, including any one or more of superficial gas velocity, aspect ratio of the catalyst bed, and catalyst particle size.

The catalyst in the reactor is maintained at a predetermined or desired density in the dense phase region during the reaction process with appropriate backmixing of catalyst flowing through the reactor. The dense bed region is considered a section of the reactor in which the catalyst solids do not substantially move axially through the reactor with the reactant gases, but rather mix randomly within the region. Preferably, the dense bed region is operated in a bubbling, slugging or turbulent fluidization regimes and, most preferably, in a turbulent fluidization regime.

In the turbulent regime, the catalyst bed preferably has a fairly well-defined "level" such that there is a relatively sharp change in the density of the bed at the transition between the dense zone and a dilute zone located above the dense phase zone. The density of the catalyst in the reactor can be defined as the volume fraction of catalyst solids in the reactor. Preferably, the catalyst in the dense phase zone is maintained at a solids volume fraction of from 0.20 to 0.55, meaning that within the dense phase 20% to 55% of the volume is occupied by solid catalyst particles. Preferably, the catalyst in the dense phase zone is maintained at a solids volume fraction of from 0.3 to 0.5, more preferably from 0.35 to 0.45.

The dilute phase zone is maintained in the reactor above the dense phase zone. Preferably, the catalyst in the dilute phase zone is maintained a solids volume fraction of not greater than 0.4, more preferably not greater than 0.3, and most preferably not greater than 0.2.

The flow of gas through the catalyst bed is sufficient to keep the bed fluidized with sufficient backmixing of solids. In this invention, the flow of gas through the catalyst bed is preferably measured according to superficial gas velocity (SGV), which is defined as volumetric flow rate of gas leaving the reactor ($m^3$/sec) divided by the average cross sectional diameter of the reactor ($m^3$). In one embodiment, the reactor is operated at a superficial gas velocity of at least 0.1 meters per second, preferably at least 0.5 meters per second. The flow should not be so high, however, such that the solids volume fraction in the dense bed drops too low. In one embodiment, the superficial gas velocity is not greater than 2 meters per second, in another not greater than 1.5 meters per second. Preferably, the reactor is maintained at a superficial gas velocity of from 0.1 to 2 meters per second, more preferably from 0.5 to 1.5 meters per second.

The catalyst in the reactor can be maintained in the fluidized state by injecting gas, e.g., the feed, into a lower portion of the reactor so as to keep the bed fluidized. Preferably, the feed gas is injected into a distributor and relatively evenly distributed so as to fluidize the catalyst in the reactor.

In order to achieve the proper level of backmixing in the dense phase bed, the aspect ratio of the catalyst bed should be kept relatively low. According to this invention, the aspect ratio is the ratio of the height of the catalyst bed to the diameter of the catalyst bed. Preferably, the dense phase bed is maintained at a catalyst bed height to diameter ratio of not greater than 10:1, more preferably not greater than 5:1, and most preferably not greater than about 2:1.

The particle size of the catalyst can also contribute to the effective fluidization and backmixing of the catalyst. In one embodiment of the invention, the catalyst bed includes catalyst particles having a particle size (i.e., average diameter) of from 20 to 300 microns. Preferably, the catalyst particles have a particle size of from 40 to 200 microns.

Backmixing of catalyst solids in the reactor should be sufficient so as to maintain a relatively low temperature differential between the top and bottom of the dense phase catalyst bed. Preferably, the dense phase catalyst bed is maintained at a temperature differential of not greater than about 50° C., more preferably not greater than about 40° C., and most preferably not greater than about 30° C.

The temperature in the dense phase fluid bed itself can be controlled in numerous ways even though it is not necessary to incorporate heat transfer means within the reactor. For example, feed preheat, throughput or catalyst volume can be controlled to accomplish the desired objectives of conversion and overall temperature.

In one embodiment of the invention, the dense phase fluidized bed is maintained at a temperature of from 150° C. to 350° C. Preferably the dense phase fluidized bed is maintained at a temperature of from 175° C. to 325° C., more preferably from 200° C. to 300° C.

In one embodiment, the temperature of the fluidized bed is maintained by controlling the feed gas entering the reactor. The temperature of the feed gas can be kept at an appropriate reactor inlet temperature as to limit the temperature within the reactor vessel. Preferably, the gas flowing through the fluid bed reactor flows into the reactor at a temperature of from 60°

C. to 95° C. More preferably the gas flowing through the fluid bed reactor flows into the reactor at a temperature of from 65° C. to 90° C., and most preferably from 70° C. to 85° C.

Since the reaction process is an exothermic process, the temperature within the reactor can be controlled by limiting the conversion of the reactants. In one embodiment, the gas flowing through the fluid bed reactor contains CO and $CO_2$, and the gas is contacted with the catalyst at a rate to control molar conversion of the CO and $CO_2$, based on the total amount of CO and $CO_2$ in the feed, in a range of from 30% to 55%. Preferably conversion of the CO and $CO_2$ is maintained in a range of from 35% to 50%, more preferably from 40% to 45%.

Because the reactor is maintained to balance the heat of the reaction with the amount of desired feed preheat, little if any internal reactor cooling is needed. In one embodiment, the reactor has an internal heat exchange surface area of not greater than 1000 $m^2$. Preferably, the reactor has an internal heat exchange surface area of not greater than 500 $m^2$, more preferably not greater than 200 $m^2$.

In another embodiment of the invention, the reactor has an internal heat exchange surface having a surface to volume ratio of not greater than 100 $m^{-1}$. Preferably, the reactor has an internal heat exchange surface having a surface to volume ratio of not greater than 50 $m^{-1}$, and more preferably not greater than 25 $m^{-1}$.

The overall reaction process can include one or more reactors. Preferably, the process includes one or more reactors, with no two reactors in series.

The gas feed entering the fluidized bed reactor system is preferably converted, partially or fully, in the fluidized zone of catalyst into a gaseous effluent. The gaseous effluent includes methanol product and generally some unreacted syngas components. Preferably, the gaseous effluent is sent to a disengaging zone or vessel so separate entrained catalyst from the gaseous components. In one embodiment, one or more cyclones are provided within the disengaging zone to separate the catalyst composition from the gaseous effluent. Preferably, the disengaging zone and cyclones are located in an upper portion of the reactor. Other methods can also be used to separate the catalyst from the gaseous components. For example, gravity effects within the disengaging vessel can also be used to separate the catalyst composition from the gaseous effluent. Other methods for separating the catalyst composition from the gaseous effluent include the use of plates, caps, elbows, and the like. The catalyst disengaged from the gaseous effluent is returned to the fluidized reaction zone, preferably directly to the dense phase fluidized bed.

II. Synthesis Gas Production

A. Methods of Making Synthesis Gas Feed

The methanol manufacturing process of this invention uses synthesis gas (syngas) as feed. Synthesis gas comprises carbon monoxide and hydrogen. Optionally, carbon dioxide and nitrogen are included.

Synthesis gas can be manufactured from a variety of carbon sources. Examples of such sources include biomass, natural gas, $C_1$-$C_5$ hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention natural gas is the preferred hydrocarbon feed source.

Any suitable syngas forming reactor or reaction system can be used in combination with the fluidized bed reaction system of this invention. Examples of synthesis gas forming systems include partial oxidation, steam or $CO_2$ reforming, or some combination of these two chemistries.

B. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \leftrightarrows CO + 3H_2 \tag{1}$$

or $$C_nH_m + nH_2O \leftrightarrows nCO + [n+(m/2)]H_2 \tag{2}$$

and $$CO + H_2O \leftrightarrows CO_2 + H_2 \tag{3 shift reaction}$$

The reaction is carried out in the presence of a catalyst. Any conventional reforming type catalyst can be used. The catalyst used in the step of catalytic steam reforming comprises at least one active metal or metal oxide of Group 6 or Group 8-10 of the Periodic Table of the Elements. The Periodic Table of the Elements referred to herein is that from *CRC Handbook of Chemistry and Physics,* $82^{nd}$ Edition, 2001-2002, CRC Press LLC, which is incorporated herein by reference.

In one embodiment, the catalyst contains at least one Group 6 or Group 8-10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with at least one promoter. Examples of promoters include alkali and rare earth promoters. Generally, promoted nickel oxide catalysts are preferred.

The amount of Group 6 or Group 8-10 metals in the catalyst can vary. Preferably, the catalyst includes from about 3 wt % to about 40 wt % of at least one Group 6 or Group 8-10 metal, based on total weight of the catalyst. Preferably, the catalyst includes from about 5 wt % to about 25 wt % of at least one Group 6 or Group 8-10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w as metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the synthesis gas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

The hydrogen to carbon oxide ratio of the synthesis gas produced will vary depending on the overall conditions of the reformer. Preferably, the molar ratio of hydrogen to carbon oxide in the synthesis gas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

C. Partial Oxidation to Make Syngas

The invention further provides for the production of synthesis gas, or CO and $H_2$, by oxidative conversion (also referred to herein as partial oxidation) of hydrocarbon, particularly natural gas and $C_1$-$C_5$ hydrocarbons. According to the process, hydrocarbon is reacted with free-oxygen to form the CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \leftrightarrows nCO + (m/2)H_2 \qquad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Tl, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Tb, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminum titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about $10^3$ cm³/g·hr to about $10^5$ cm³/g·hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO+H_2O \leftrightarrows H_2 + CO_2$. This reaction occurs simultaneously with the oxidative conversion of the hydrocarbon in the feed to CO and $H_2$ or synthesis gas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65:1, with oxygen-to-carbon ratios in the region of the stoichiometric ratio of 0.5:1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

D. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two synthesis gas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form synthesis gas. In the fixed bed syngas generation process, hydrocarbon feed and oxygen or an oxygen-containing gas are introduced separately into a fluid catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5:1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

III. Syngas Feed to the Fluidized Bed Reactor

Synthesis gas (syngas) is used in the feed to the fluidized bed reaction system of this invention. Desirably, the synthesis gas feed (including any recycle syngas recovered from the process itself as well as fresh syngas) has a molar ratio of hydrogen ($H_2$) to carbon oxides ($CO+CO_2$) in the range of from about 0.5:1 to about 20:1, preferably in the range of from about 1:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas, and preferably less than 20% by weight, more preferably less than 10% by weight.

Desirably, the stoichiometric molar ratio is sufficiently high so as maintain a high yield of methanol, but not so high as to reduce the volume productivity of methanol. Preferably, the synthesis gas fed to the methanol synthesis process has a stoichiometric molar ratio (i.e., a molar ratio of $(H_2-CO_2)/(CO+CO_2)$) of from about 1.0:1 to about 2.7:1, more preferably from about 1.5 to about 2.5, more preferably a stoichiometric molar ratio of from about 1.7:1 to about 2.5:1.

IV. Catalyst

Preferably, the methanol synthesis catalyst used in the process of this invention includes an oxide of at least one element selected from the group consisting of copper, silver, zinc, boron, magnesium, aluminum, vanadium, chromium, manganese, gallium, palladium, osmium and zirconium. More preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

V. Recovery and Further Processing of Methanol Product

The methanol product from the fluidized bed reactor is generally sent to a separation unit or vessel to remove light product having a higher boiling point than the methanol. This separation preferably yields a liquid product rich in methanol, although the separated methanol product can include other components such as water. The separated methanol product can be used "as is," or it can be further processed if desired. Processing can be accomplished using any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol present.

In one embodiment, the separated and recovered methanol product is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another embodiment, the separated recovered methanol product is sent from the methanol synthesizing unit or vessel to a distillation system. The distillation system contains one or more distillation columns which are used to further separate the desired methanol composition from water and hydrocarbon by-product streams. Desirably, the methanol composition that is separated from the crude methanol comprises a majority of the methanol contained in the methanol product prior to separation.

In one embodiment, the distillation system includes a step of treating the recovered methanol product steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles are taken overhead and methanol liquid as bottoms. The second is a "rectifying column" from which methanol product is taken as an overhead stream or at a high level, and water is removed as a bottoms stream. In this embodiment, the rectifying column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water or aqueous methanol is taken as a bottoms stream.

Alternatively, undesirable by-products are removed from the separated methanol stream from the methanol synthesis reactor by adsorption. In such a system, other components such as fusel oil can be recovered by regenerating the adsorbent.

VI. Use of the Methanol Composition in the Manufacture of Olefins

The methanol product composition of this invention can be used as feed for any conventional process. Examples of such uses include the manufacture of methyl tertiary butyl alcohol (MTBE) for use in reformulated gasolines and oxygenated fuels, the use of methanol as a fuel for fuel cells, use as feedstock to make olefins, and for use in making acetic acid and formaldehyde.

The methanol product stream of this invention is particularly suited for conversion to olefins, particularly ethylene and/or propylene. The methanol product stream can be fed directly to an olefin conversion process or it can be transported in large quantities over great distances and converted to olefins.

According to this invention, the methanol product can be produced in large scale quantities for conversion to olefins, which is of great advantage for further conversion of the olefins to polyolefins such as polyethylene and polypropylene. Advantageously, this invention allows for at least 100,000 metric tons of methanol product per year. Preferably, production is at least 500,000 metric tons per year, more preferably at least 1 million metric tons per year, and most preferably at least 2 million metric tons per year.

In one embodiment, the methanol stream of the invention is separated from a crude methanol stream, and transported to a location geographically distinct from that where the methanol composition was separated from the crude methanol stream. Preferably, the methanol composition of this invention is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to an olefin conversion unit for conversion to an olefin product. The methanol composition is preferably, loaded onto a ship, with the ship able to contain at least 20,000 tons, preferably at least 40,000 tons, and more preferably at least 80,000 tons.

An advantage of being able to transport the methanol composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. Methanol is routinely transported in vessels that are similar to those that transport crude oil and other fuels. Examples of locations of remote gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

VII. EXAMPLES

Example 1

A conventional tubular methanol synthesis reaction system is shown in FIG. 1. In accordance with the system in FIG. 1, syngas is sent to a compressor C-1, and the compressed gas is then sent to a heat exchanger E-1 to preheat the compressed syngas. The preheated feed is then sent to a tubular reactor R-1, where the syngas components are converted into methanol. The reactor R-1 is kept cool by supplying water, and the water is converted to steam.

Methanol product leaves the reactor R-1 and is sent to heat exchanger E-1 to preheat the syngas feed. The methanol product is further cooled in heat exchanger E-2, and then sent to separator S-1, where unreacted syngas components are separated from the methanol. A portion of the separated gas components is purged and a portion is added back to the syngas feed and sent to the compressor C-1.

This process was simulated using PRO/II ver. 6.0 software, with a capacity based on 1000 kg-mole/hr of synthesis gas. The corresponding material balance information is shown in Table 1.

TABLE 1

| Steam Description | Syngas Makeup to C-1 | Syngas from C-1 to E-1 | Syngas from E-1 to R-1 | Product Effluent from R-1 to E-1 | Product from E-1 to E-2 | Purge from S-1 | Methanol from S-1 |
|---|---|---|---|---|---|---|---|
| Phase | Vapor | Vapor | Vapor | Vapor | Mixed | Vapor | Mixed |
| Temperature (° C.) | 152.6 | 60.4 | 220.0 | 250.0 | 98.2 | 38.0 | 38.0 |
| Pressure (bar) | 85 | 85 | 85 | 85 | 85 | 85 | 85 |
| Flowrate (kg-mol/hr) | 999.8 | 499.8 | 499.8 | 4411.5 | 4411.5 | 62.8 | 348.7 |
| Total Mass Rate (kg/hr) | 11125 | 45499 | 45499 | 45499 | 45499 | 540.5 | 10551 |
| Molar Composition (%) | | | | | | | |
| Methane | 1.18 | 11.76 | 11.76 | 13.35 | 13.35 | 14.43 | 0.81 |
| CO | 25.68 | 10.14 | 10.14 | 5.78 | 5.78 | 6.27 | 0.09 |
| $CO_2$ | 5.14 | 4.00 | 4.00 | 3.57 | 3.57 | 3.71 | 1.86 |
| $H_2$ | 67.50 | 69.84 | 69.84 | 64.85 | 64.85 | 70.38 | 0.32 |
| $H_2O$ | 0.19 | 0.10 | 0.10 | 1.07 | 1.07 | 0.08 | 12.62 |
| $O_2$ | 0.00 | 0.00 | 0.00 | 0.00 | 0.00 | 0.00 | 0.00 |
| Methanol | 0.00 | 0.53 | 0.53 | 7.27 | 7.27 | 0.66 | 84.25 |
| $N_2$ | 0.31 | 3.63 | 3.63 | 4.12 | 4.12 | 4.47 | 0.06 |

The heat transfer duties are as follows:

| | |
|---|---|
| E-1 Feed/Effluent Exchanger | 2.54e07 kJ/hr |
| E-2 Final Effluent Cooler | 1.84e07 kJ/hr |
| R-1 Tubular Methanol Synthesis Reactor | 2.28e07 kJ/hr |

The heat transfer surface area for exchangers E-1 and E-2 can be estimated assuming a heat transfer coefficient of 428 J $m^{-2}$ $s^{-1}$° $K^{-1}$ (75 Btu $hr^{-1}$ $ft^{-2}$° $F.^{-1}$) and using the temperatures shown in Table 1 (Coolant temperature for E-2 assumed to be 30° C.). The resulting surface area is 488 $m^2$ for E-1 and 474 $m^2$ for E-2.

The reactor can be sized based on process conditions at the reactor exit and on the following assumptions:

| | |
|---|---|
| Axial pressure drop | 22.3 kPa $m^{-1}$ (1.0 psi $ft^{-1}$) |
| Catalyst particle diameter | 5 mm |
| Catalyst bulk density | 1100 kg $m^{-3}$ |
| Catalyst particle density | 2000 kg $m^{-3}$ |
| Gas Density | 19.3 kg $m^{-3}$ |
| Gas viscosity | 2.0e-05 kg $m^{-1}$ $s^{-1}$ |

-continued

| Tube diameter | 0.0254 m (1 inch) |
| Tube spacing and pitch | 1.25" triangular |

Based on this tube geometry, 44% of the cross sectional area of the reactor contains catalyst and the outside specific surface area is 91.3 m²/m³. The reactor diameter that meets the axial pressure drop criteria is 1.62 m.

The catalyst volume required can be calculated from the following kinetic model (Szarawara, J. and Reychman, K., 1980. *Int. Chem. Proc.*, 1: 331):

dense/turbulent bed flow regime that achieves a high internal circulation rate of the solid catalyst, creating a close approach to an isothermal temperature profile. The high solids circulation rate also induces gas recirculation, achieving a close approach to a perfectly mixed gas phase, or continuous stirred tank reactor (CSTR) operation. In this configuration, hot reactor effluent stream is used to generate low pressure (1.7 bar) steam in exchanger E-3. Warm reactor effluent leaving E-3 is used to preheat the reactor feed in exchanger E-4. The reaction temperature is controlled by controlling the amount of feed preheat in E-4. The material balance is shown in Table 2.

TABLE 2

| Steam Description | Syngas Makeup to C-2 | Syngas from C-2 to E-4 | Effluent from R-2 to E-3 | Recycle Syngas from S-2 to C-2 | Purge from S-2 | Methanol from S-2 | Syngas from E-4 to R-2 | Product from E-3 to E-4 | Product from E-4 to E-5 |
|---|---|---|---|---|---|---|---|---|---|
| Phase | Vapor | Vapor | Vapor | Vapor | Vapor | Mixed | Vapor | Vapor | Vapor |
| Temperature (° C.) | 152.6 | 60.3 | 250.1 | 38.0 | 38.0 | 38.0 | 77.0 | 107.5 | 125.0 |
| Pressure (bar) | 85 | 85 | 85 | 85 | 85 | 85 | 85 | 85 | 85 |
| Flowrate (kg-mol/hr) | 999.8 | 5000 | 4410 | 4000 | 60 | 350 | 5000 | 4410 | 4410 |
| Total Mass Rate (kg/hr) | 11125 | 46499 | 46418 | 35295 | 533 | 10590 | 46499 | 46418 | 46418 |
| Molar Composition (%) | | | | | | | | | |
| Methane | 1.18 | 12.05 | 13.63 | 14.74 | 14.74 | 0.83 | 12.05 | 13.63 | 13.63 |
| CO | 25.68 | 10.31 | 5.96 | 6.46 | 6.46 | 0.09 | 10.31 | 5.96 | 5.96 |
| CO$_2$ | 5.14 | 4.14 | 3.73 | 3.89 | 3.89 | 1.94 | 4.14 | 3.73 | 3.73 |
| H$_2$ | 67.50 | 69.03 | 64.00 | 69.49 | 69.49 | 0.32 | 69.03 | 64.00 | 64.00 |
| H$_2$O | 0.19 | 0.10 | 1.07 | 0.08 | 0.08 | 12.61 | 0.10 | 1.07 | 1.07 |
| O$_2$ | 0.00 | 0.00 | 0.00 | 0.00 | 0.00 | 0.00 | 0.00 | 0.00 | 0.00 |
| Methanol | 0.00 | 0.53 | 7.29 | 0.67 | 0.67 | 84.15 | 0.53 | 7.29 | 7.29 |
| N$_2$ | 0.31 | 3.84 | 4.31 | 4.68 | 4.68 | 0.06 | 3.84 | 4.31 | 4.31 |

$$CO + 2H_2 \leftrightarrow CH_3OH \quad (1)$$

$$CO_2 + 3H_2 \leftrightarrow CH_3OH + H_2O \quad (2)$$

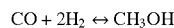

$$r_1 = 0.2032 \exp\left(\frac{-2954}{T}\right) p_{CO}^{0.5} p_{H2} \left(1 - \frac{p_{CH3OH}}{K_1 p_{CO} p_{H2}^2}\right) \quad (3)$$

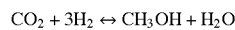

$$r_1 = 8.893 \times 10^{-3} \exp\left(\frac{-6163}{T}\right) p_{CO2}^{0.5} p_{H2}^{1.5} \left(1 - \frac{p_{CH3OH}}{K_2 p_{CO2} p_{H2}^3}\right) \quad (4)$$

where the reaction rates are in kg-mol kg$_{cat}^{-1}$ h$^{-1}$, the partial pressures are in bar, the temperature is in ° K, and K$_1$ and K$_2$ are the equilibrium constants for reactions (1) and (2).

Integration of these rate expressions at a constant 250° C. temperature for a plug flow reactor yields a catalyst requirement of 3044 kg, or a volume 2.77 m³. This requires a reactor tube length of 3.04 m. The heat transfer surface area contained within this reactor is 575 m².

Example 2

Figure 2:
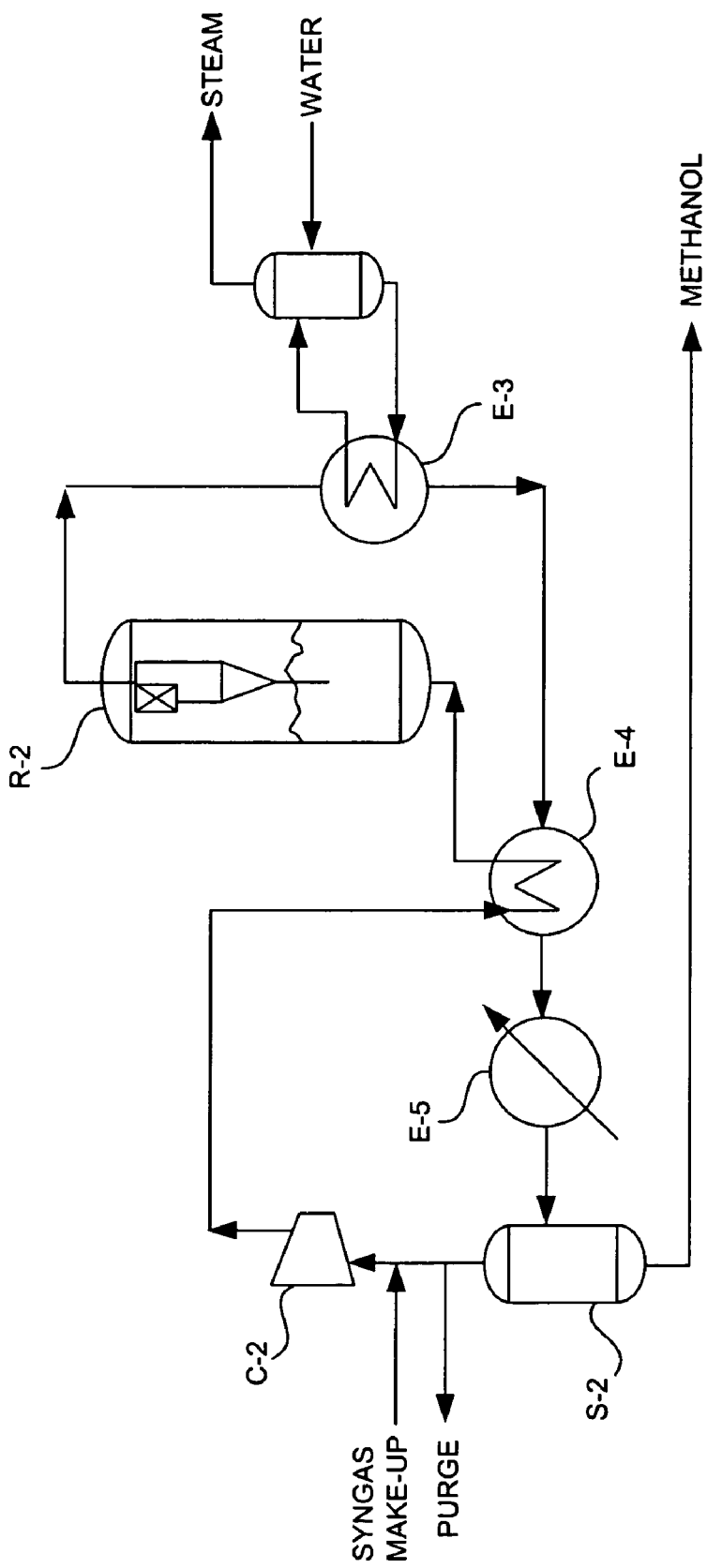
FIG. 2 shows an example of a turbulent/dense fluid bed reactor system of the invention in which the reactor includes no internal cooling means or devices.

FIG. 2 shows a process flow configuration for methanol synthesis utilizing a fluid bed synthesis reactor R-2 that does not externally cool the reaction. The feed basis is the same as in Example 1. The fluid bed reactor R-2 is operated in a The heat transfer duties are as follows:

| E-3 Waste heat boiler | 1.91e07 kJ/hr |
| E-4 Feed/Effluent Exchanger | 0.26e07 kJ/hr |
| E-5 Final Effluent Cooler | 2.21e07 kJ/hr |

Using the same assumptions for the heat exchangers as in Example 1, the following surface areas are calculated:

| E-3 Waste heat boiler | 249 m² |
| E-4 Feed/Effluent Exchanger | 35.5 m² |
| E-5 Final Effluent Cooler | 514 m² |

The reactor diameter is sized based on the desired gas superficial velocity. A velocity of 1 m/sec was selected to achieve turbulent fluidization with good gas-solid contacting and high internal solid circulation to achieve a high degree of gas backmixing. These properties achieve isothermal operation with constant gas composition throughout the reaction zone. The reactor diameter required for 1 m/sec superficial gas velocity is 0.92 m.

The same kinetic model of Example 1 is used to determine the catalyst volume required. Due to the gas backmixing, the average reactant concentrations are lower in the backmixed case compared to the plug flow case. A larger catalyst weight of 3875 kg is required for the fluid bed case. At the superficial velocity of 1 m/sec, the solids fraction in the dense portion of the fluid bed is about 0.4. The calculated height of catalyst in the dense portion of the bed is 7.24 m. The height of the "freeboard" section of the bed is determined by the cyclone pressure drop and other factors, and is typically about 15 m, for an overall height of 22.2 m.

The data from Example 1 and Example 2 are summarized and shown in Table 3:

TABLE 3

|  | Example 1 | Example 2 |
| --- | --- | --- |
| Steam generating Exchanger | | |
| Item number | R-1 | E-3 |
| Duty, kJ/hr | 2.28e07 | 1.91e07 |
| Surface area, m$^2$ | 575 | 249 |
| Feed/Effluent Exchanger | | |
| Item number | E-1 | E-4 |
| Duty, kJ/hr | 2.54e07 | 0.26e07 |
| Surface area, m$^2$ | 488 | 36 |
| Final cooler | | |
| Item number | E-2 | E-5 |
| Duty, kJ/hr | 2.28e07 | 2.21e07 |
| Surface area, m$^2$ | 474 | 514 |
| TOTAL EXCHANGER SURFACE m$^2$ | 1537 | 799 |
| Reactor Item Number | R-1 | R-2 |
| Diameter, m | 1.62 | 0.92 |
| Height of reaction zone, m | 3.04 | 7.24 |
| Volume of reaction zone, m$^3$ | 6.27 | 4.81 |
| Total reactor height, m | 3.04 | 22.2 |
| Total reactor volume, m$^3$ | 6.27 | 14.8 |
| Number of 1" diameter tubes | 2360 | 0 |

The system of Example 2 requires just 52% of the heat transfer surface area (799 m$^2$) as the Example 1 system (1537 m$^2$). In addition, the reactor of Example 2 does not have any heat transfer surface contained within the reaction vessel. It is mostly an empty vessel, containing only a gas distribution grid and cyclones for keeping catalyst within the reactor. The diameter of the Example 1 reactor is also significantly larger (by 76%) than the Example 2 reactor. Reactors with significantly larger diameters are particularly more difficult and expensive to build and operate at commercial scales.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:

1. A process for making methanol product in a fluid bed reactor, comprising:
   flowing a gas containing carbon monoxide and hydrogen through a fluid bed reactor at a superficial gas velocity of at least 0.1 meter per second and not greater than 2 meters per second, the fluid bed reactor consisting essentially of an empty vessel having an internal heat exchange surface having a surface to volume ratio of not greater than 100 m$^{-1}$;
   contacting the gas with methanol synthesis catalyst in a dense phase fluidized bed having a catalyst bed height to diameter ratio of not greater than 10:1 so as to form methanol product; and
   separating the catalyst from the methanol product in an upper portion of the reactor.

2. The process of claim 1, wherein the catalyst has a particle size of from 20 to 300 microns.

3. The process of claim 1, wherein the catalyst in the dense phase bed is maintained at a solids volume fraction of from 0.20 to 0.55.

4. The process of claim 1, wherein the catalyst in the dense phase bed is maintained at a solids volume fraction of from 0.3 to 0.5.

5. The process of claim 1, wherein a dilute phase zone is maintained in the reactor above the dense phase zone and the dilute phase is maintained at a solids volume fraction of not greater than 0.4.

6. The process of claim 1, wherein the dense phase catalyst bed is maintained at a temperature differential of not greater than about 50° C.

7. The process of claim 1, wherein the process includes one or more reactors with no two reactors in series.

8. The process of claim 1, wherein the catalyst that is separated from the methanol product is returned to the dense phase fluidized bed.

9. The process of claim 1, wherein the methanol synthesis catalyst includes an oxide of at least one element selected from the group consisting of copper, silver, zinc, boron, magnesium, aluminum, vanadium, chromium, manganese, gallium, palladium, osmium and zirconium.

10. The process of claim 1, wherein the dense phase fluidized bed is maintained at a temperature of from 150° C. to 350° C.

11. The process of claim 1, wherein the gas flowing through the fluid bed reactor flows into the reactor at a temperature of from 60° C. to 95° C.

12. The process of claim 1, wherein the gas flowing through the fluid bed reactor further contains $CO_2$, and the gas is contacted with the catalyst at a rate to control molar conversion of the CO and $CO_2$, based on the total amount of CO and $CO_2$ in the feed, in a range of from 30% to 55%.

13. A process for making methanol product in a fluid bed reactor, comprising:
   contacting a gas containing carbon monoxide and hydrogen with methanol synthesis catalyst in a dense phase fluidized bed at a superficial gas velocity of not greater than 2 meters per second to form methanol product, wherein the fluidized bed has a height to diameter ratio of not greater than 10:1, the fluid bed reactor consisting essentially of an empty vessel having an internal heat exchange surface having a surface to volume ratio of not greater than 100 m$^{-1}$;
   separating the catalyst from the methanol product in an upper portion of the reactor; and
   returning the catalyst that is separated from the methanol product to the dense phase fluidized bed.

14. The process of claim 13, wherein the catalyst in the dense phase bed is maintained at a solids volume fraction of from 0.20 to 0.55.

15. The process of claim 13, wherein the dense phase catalyst bed is maintained at a temperature differential of not greater than about 50° C.

16. The process of claim 13, wherein the catalyst that is separated from the methanol product is returned to the dense phase fluidized bed.

17. The process of claim 13, wherein the methanol synthesis catalyst includes an oxide of at least one element selected from the group consisting of copper, silver, zinc, boron, magnesium, aluminum, vanadium, chromium, manganese, gallium, palladium, osmium and zirconium.

18. The process of claim 13, wherein the dense phase fluidized bed is maintained at a temperature of from 150° C. to 350° C.

19. The process of claim 13, wherein the gas flows into the reactor at a temperature of from 60° C. to 95° C.

20. The process of claim 13, wherein the gas further contains $CO_2$, and the gas is contacted with the catalyst at a rate to control molar conversion of the CO and $CO_2$, based on the total amount of CO and $CO_2$ in the feed, in a range of from 30% to 55%.

21. A process for making methanol product in a fluid bed reactor, comprising:

contacting a gas containing carbon monoxide and hydrogen with methanol synthesis catalyst at a superficial gas velocity of not greater than 2 meters per second to form methanol product, wherein the catalyst is maintained as a fluidized bed having a height to diameter ratio of not greater than 10:1, the fluid bed reactor consisting essentially of an empty vessel having an internal heat exchange surface having a surface to volume ratio of not greater than 100 $m^{-1}$;

separating the catalyst from the methanol product; and returning the catalyst that is separated from the methanol product to the fluidized bed.

22. The process of claim 21, wherein the catalyst in the fluidized bed is a dense phase fluidized bed maintained at a solids volume fraction of from 0.20 to 0.55.

23. The process of claim 21, wherein the catalyst that is separated from the methanol product is returned to the fluidized bed.

24. The process of claim 21, wherein the fluidized bed is maintained at a temperature of from 150° C. to 350° C.

25. The process of claim 21, wherein the gas flows into the reactor at a temperature of from 60° C. to 95° C.

26. The process of claim 21, wherein the gas further contains $CO_2$, and the gas is contacted with the catalyst at a rate to control molar conversion of the CO and $CO_2$, based on the total amount of CO and $CO_2$ in the feed, in a range of from 30% to 55%.

* * * * *